United States Patent [19]

Taylor

[11] Patent Number: 5,457,891
[45] Date of Patent: Oct. 17, 1995

[54] LEG ANGLE MEASUREMENT GAUGE

[75] Inventor: Dean A. Taylor, Vancouver, Canada

[73] Assignee: Generation II Orthotics, Inc., Richmond, Canada

[21] Appl. No.: 210,590

[22] Filed: Mar. 18, 1994

[51] Int. Cl.⁶ .............................. A61B 5/103; G01B 1/00
[52] U.S. Cl. ................... 33/512; 33/534; 128/774
[58] Field of Search ........................ 33/511, 512, 515, 33/534, 558.01, 558.04, 558.05, 1 N; 128/774, 782

[56] References Cited

U.S. PATENT DOCUMENTS

| 3,358,373 | 12/1967 | Martin | 33/512 |
|---|---|---|---|
| 3,815,247 | 6/1974 | Debrunner | 33/512 |
| 3,902,482 | 9/1975 | Taylor | 128/80 |
| 4,804,001 | 2/1989 | McLeod, Jr. | 128/782 |
| 4,940,063 | 7/1990 | Challis | 33/534 |
| 4,989,337 | 2/1991 | Mason et al. | 33/512 |
| 5,121,753 | 6/1992 | Paez | 33/515 |
| 5,135,469 | 8/1992 | Castillo | 602/16 |
| 5,148,606 | 9/1992 | Mason et al. | 33/512 |
| 5,163,228 | 11/1992 | Edwards et al. | 33/512 |
| 5,220,308 | 6/1993 | Batzdorff et al. | 340/573 |
| 5,277,698 | 1/1994 | Taylor | 602/26 |

FOREIGN PATENT DOCUMENTS 3100060   8/1982   Germany .................. 128/774

Primary Examiner—William A. Cuchlinski, Jr.
Assistant Examiner—G. Bradley Bennett
Attorney, Agent, or Firm—Christie, Parker & Hale

[57] ABSTRACT

A gauge to measure the lateral inclination of a part of a brace above a patient's knee relative to a part of the brace below the patient's knee. The brace has a hinge to allow flexing of the knee. The gauge has a calibrated body that can be attached to the hinge of the brace. Limbs extend from each end of the body. There is a pivotal joint to allow each limb to pivot relative to the calibrated body. There is a reciprocable extension at the outer most end of each limb that is able to extend to contact the brace. A marker extends from the inner end of the limbs to indicate on the calibrated body the inclination of each limb. In this way the extension can be reciprocated to contact the brace and a reading them made of each marker on the calibrated scale to determine the inclination of each limb of the gauge and thus of the knee.

14 Claims, 3 Drawing Sheets

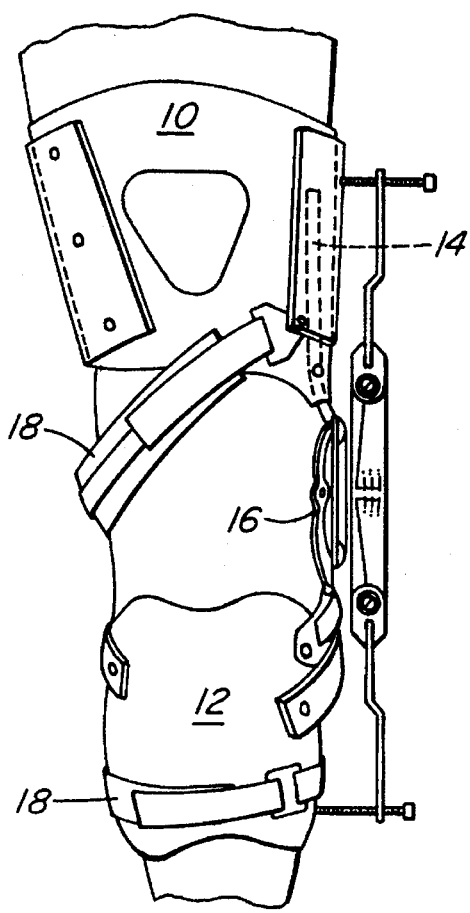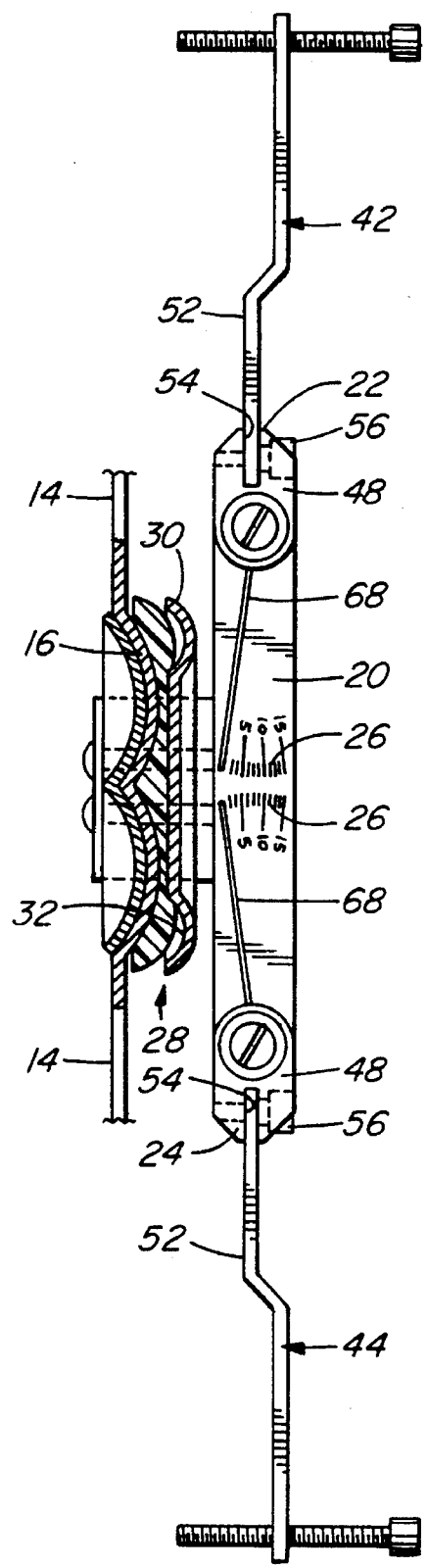
FIG. 1
FIG. 2

LEG ANGLE MEASUREMENT GAUGE

FIELD OF THE INVENTION

This invention relates to a gauge to measure the lateral inclination of a part of a brace above a patient's knee relative to a part of a brace below the patient's knee.

DESCRIPTION OF THE PRIOR ART

Braces for the knee, both post-operative and as a general support where weakness of the knee is observed, are well known. They have become popular because they provide excellent support and yet are light in weight and unobtrusive to wear. It is common to see people taking part in athletic events, for example tennis and skiing, wearing these knee braces without any apparent hindrance to performance.

These braces find application in a number of circumstances. For example, they are used to treat uni-compartmental osteoarthritis and for post-operative use following high tibial osteotomy (HTO) as discussed below. They are also used to support the knee when ligaments are damaged. The ligaments can heal while the brace removes at least some of the stress from them.

Uni-compartmental osteoarthritis may occur in the medial or in the lateral compartment of the knee. It is a malfunction of the knee where uneven distribution of pressure occurs across the knee. This uneven distribution produces excessive wear on the inside of the knee joint in medial compartmental osteoarthritis and on the outside of the knee joint in a lateral compartmental osteoarthritis. A healthy knee joint has an even distribution of pressure medially and laterally and the space between the femur and the tibia is symmetrical and approximately one quarter inch. If uni-compartmental osteoarthritis is induced, for example by injury or by aging, the space between the femur and the tibia decreases. The problem may progress to the extent that the space is eliminated and the femur contacts the tibia. Erosion of the tibia may result.

With uni-compartmental osteoarthritis there is a change in the normal angle between the femur and the tibia. For example, if the patient stands in 2° of varus, or bow-leggedness, then with the advancement of the disease the angle may increase to, for example, about 5° varus. Debilitation of the knee continues and the angle is increased further.

A non-invasive treatment of uni-compartment osteoarthritis is described and claimed in U.S. Pat. No. 5,277,698 issued Jan. 11, 1994. That method comprises applying a force to the knee as the knee is extended. Force is applied to that side of the knee remote from the compartment having osteoarthritis. The force is applied at about 10° to 15° posterior at the normal axes of rotation of the knee.

This method has a great virtue of being a treatment but may not be applicable in all cases, for example, where the disease has progressed too far. In those circumstances, high tibial osteotomy (HTO) or total knee arthroplasty (TKA) or knee replacement may be required.

High tibial osteotomy involves the removal of a triangular segment of the tibia as a means of correcting the excessive inclination induced by uni-compartmental osteoarthritis. Using present techniques, after surgery the knee is encased in a cast that immobilizes the knee until the bone heals.

U.S. Pat. No. 3,902,482 issued Sep. 2, 1975 relates to an orthopaedic brace having portions attachable to parts of a wearer's body on opposite sides of a body joint. There is a mechanical joint comprising a bearing plate on an end of each brace portion near the body joint. A link extends across the body joint and has a bearing plate on each end. The bearing plates of the link overlap the bearing plates of the brace portion to provide dual bearings. A pivot interconnects the bearing plates of each of the dual bearings. The pivot provides each of the dual bearings with a plurality of transverse pivotal axes, which are shiftable to accommodate the natural pivotal movement of the body joint. This arrangement is such that one of the brace portions is movable away from and toward the other of the brace portions as the body joint is flexed and straightened.

Braces of this type have achieved excellent acceptance. They are usually custom made for a patient. They are light and unobtrusive to wear. Although the pivot is light and simple in .construction, it has excellent ability to follow the relatively complex motion of the knee, unlike the braces that preceded it.

Since the above United States patent issued a substantial number of sophisticated orthopaedic braces have come onto the market. The most recent prior art known to applicant is U.S. patent application Ser. No. 170,847 filed Dec. 21, 1993. That patent application describes and claims an orthopaedic brace comprising a pair of arms to be secured to a wearer's body. There is a pivotal joint between the arms to allow pivoting of the knee while supporting the knee. There is a joint in the brace to allow control of the medial and lateral inclination of each arm relative to the pivotable joint.

U.S. patent application Ser. No. 120,261 describes and claims an orthopaedic knee brace with an anti-friction mechanical joint. This latter knee brace includes first and second cams that move within cavities. There are at least two cylindrical rollers in the cavities. These rollers fit between the internal surface of the cavities and the external peripheral surface of the cams. The shape of the cams and the shape of the cavities permit multiple access pivotal movement with the mechanical joints substantially corresponding to any movement of the wearer between a flexed position and an extended position of the knee.

There are thus substantial improvements being made all the time in orthopaedic braces. However all of these braces must be fitted. They are custom made and, particularly when used as a post-operative brace, the fitting must be carried out with great precision.

Using, for example, the brace of U.S. patent application Ser. No. 170,847 referred to above, in a patient who has undergone high tibial osteotomy, the procedure is as follows. Prior to surgery the patient will be fitted with a brace that is custom made. This means that the cuffs that are a feature of these braces will be molded to match the patient's leg. There is a cuff below the knee and a cuff above the knee. The arms that extend from the central hinge that are attached to the cuffs, are made of the appropriate length and the fitter will ensure that the central hinge is in the proper position relative to the patient's knee.

After the operation the surgeon will attempt to adjust the brace in precisely the correct manner for that patient to ensure that the correct adjustment is applied to support the knee following surgery. The surgeon can apply varus or valgus as deemed fit. The brace of the above U.S. patent application Ser. No. 170,847 is particularly useful for this adjustment but, at the moment, the measurement of the inclination is normally carried out by a relatively crude practice. No measurement of the leg is carried out and, in fitting the brace it is common to adjust until the patient is caused pain or some such purely arbitrary arrangement. It is much to be preferred that an accurate measurement be possible and that the shape of the leg be measured accurately and an accurate record kept to facilitate adjustment and, in particular, to facilitate precise adjustment.

SUMMARY OF THE INVENTION

The present invention seeks to provide a gauge that can carry out these measurements with great ease.

Accordingly, the present invention provides a gauge to measure the lateral inclination of a part of a brace above a patient's knee relative to a part of the brace below the patient's knee, the brace including a hinge to allow flexing of the knee, the gauge comprising, a calibrated body having opposed ends; means to attach the calibrated body to the hinge of the brace; first and second limbs extending one from each of said opposed ends; a pivotal joint to allow each limb to pivot relative to said calibrated body; a reciprocable extension at a distal end of each limb, able to extend to contact said brace; a marker extending from each limb to indicate on said calibrated body the inclination of each limb; whereby the extension can be reciprocated to contact the brace and a reading then made of each marker on the calibrated scale to determine the inclination of each limb of the gauge.

In one embodiment the calibrated body is a box formed with an opening with calibrations at the opening.

In a preferred embodiment the calibrated body is laminar with bosses at each end of the body to receive the limb and to allow the limb to pivot on the boss.

DESCRIPTION OF THE DRAWINGS

The invention is illustrated in the drawings in which:

FIG. 1 is an illustration of a knee brace with a gauge according to the present invention in place;

FIG. 2 is an enlarged view of the brace shown in FIG. 1;

DESCRIPTION OF THE PREFERRED EMBODIMENTS

Figure 3:
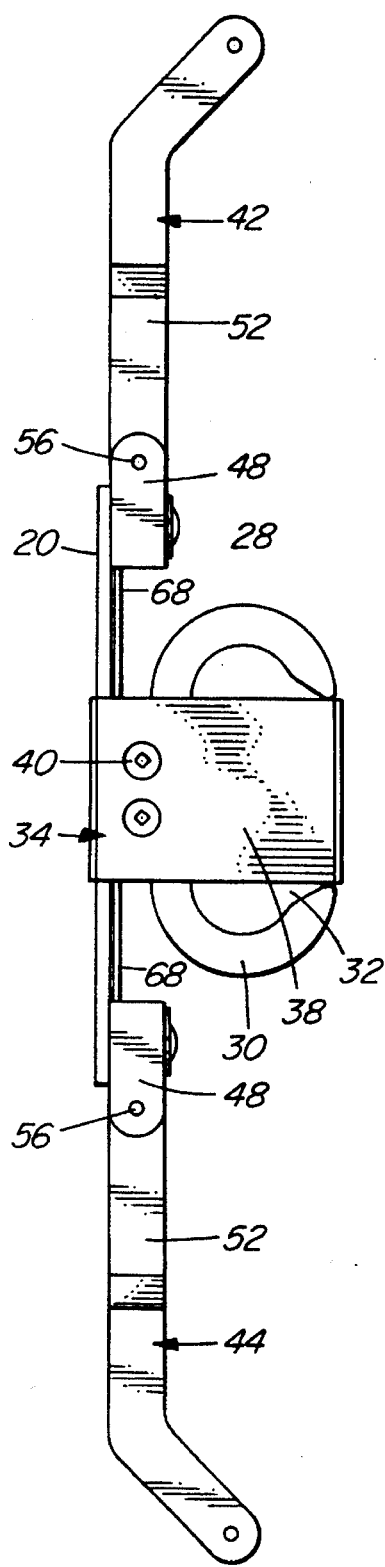
FIG. 3 is a side elevation of FIG. 2.

The drawings show a gauge to measure the lateral inclination of a part of a brace above a patient's knee relative to a part of a brace below the patient's knee. FIG. 1 is a illustration of a brace, for example the brace of the United States patents referred to above. The brace comprises an upper cuff 10 and a lower cuff 12, the latter below the knee the former above the knee. There are arms 14 extending upwardly and downwardly from a hinge 16 which is of a characteristic shape. Straps 18 extend from the cuffs 10 and 12 around the knee to provide the necessary support.. The cuffs 10 and 12 are typically of a relative hard plastic, usually polyethylene.

Figure 4:
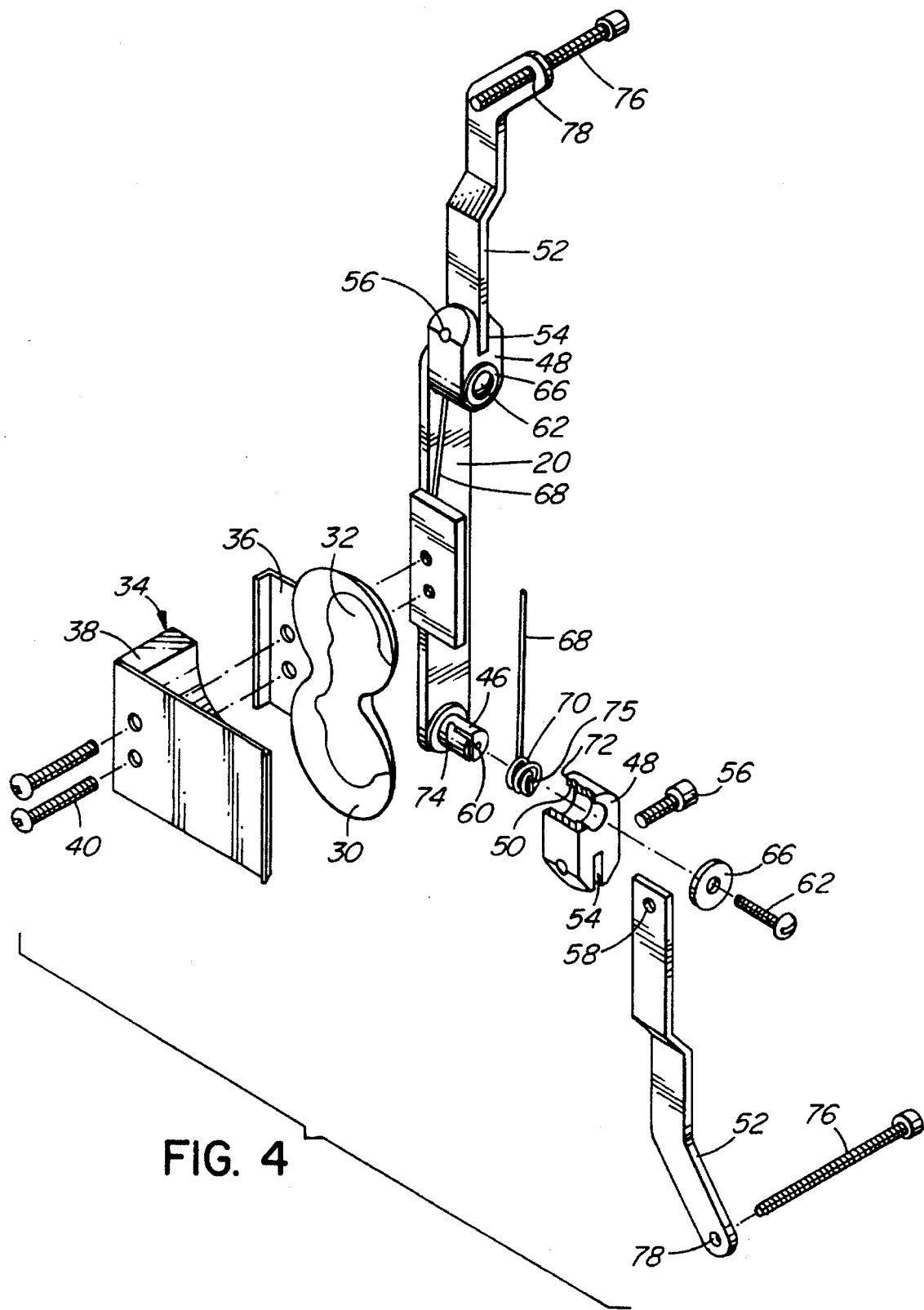
FIG. 4 is an exploded view of the brace of FIGS. 2 and 3.

As shown particularly in FIG. 2 the gauge comprises a calibrated body 20 with opposed ends 22 and 24. In the embodiment of FIGS. 2 and 3 the body 20 is laminar and there are calibrations or scales 26 marked at the middle of the body 20. There are means to attach the calibrated body 20 to the hinge 16 of the brace. In the drawings, this means comprises a shaped member 28 that is shaped to seat on the hinge 16 of the brace. To this end it has a peripheral flange 30 with recesses 32 that match the external shape of the hinge 16 as shown most clearly in FIGS. 2 and 4.

There is a bracket 34 that extends around the hinge to maintain the shaped member 28 in contact with the hinge 16. The bracket 34 comprises a generally L-shaped extension 36 extending from the shaped member 28 and a larger, also L-shaped, member 38 secured to the first L-shaped member 36 by screws 40. The result is a U-shaped member that extends around the= hinge 16 and seats on the hinge.

A first limb 42 extends from one end 22 of the calibrated body 20 and a second limb 44 extends from the other end 24 of the calibrated body 20. There is a pivotal joint to allow each limb 42 and 44 to pivot relative to the calibrated body 20. In the embodiments of FIGS. 1 to 4 the pivotal joint comprises bosses 46 (see FIG. 4) at each end of the body 20. Each limb 42 and 44 comprises a hub 48 that is provided with a recess 50 to enable the hub 48 to be received on a boss 46. In the embodiment of FIGS. 1 to 4 the limb is formed in two parts, namely the hub 48 and a lever 52 that is releasably attached to the hub 48 by the provision of a slot 54 in the hub 48 and a screw 56 extending through that slot 54, through a clear opening 58 in the lever 52.

A marker extends from each limb 42 and 44 to the calibrations 26. In the embodiments of FIGS. 1 to 4, the marker comprises a coil spring having an elongated portion 68 extending from a coil 70. The coil 70 is housed in a recess 72 in the hub 48 and on the boss 46. Portion 68 extends up through a recess 72 in the hub 48 and is anchored relative to the boss 46 by the provision of a slot 74 in the hub 48 and a chord member 75 the coil 70 to engage the slot 74.

Using this arrangement movement of the hub 48 on the boss 46, moves a marker relative to the calibrations 26 to provide a reading.

There is a reciprocable extension at the end of each limb 42 and 44 remote from the body 20. These extensions are able to extend to contact the brace, as shown in FIG. 1. In the illustrated embodiment the reciprocable extensions are screws 76 extending through threaded openings 78 at each distal end of the limbs.

Hubs 48 are attached to the bosses 46 by the provision of a threaded opening 60 in the bosses 46. A screw 62 extends through a clear opening 64 in the hub 48 to engage the threaded opening 60. A washer 66 is used as it is, of course, intended that the hub 48 move on the boss 46.

Use of the embodiments of FIGS. 1 to 4 is illustrated in FIG. 1. It can be seen that reciprocation of a screw 76, when in contact with a cuff 10 or 12, will move a limb 42 or 44 to pivot a hub 48. A portion 68 of a marker will then move on the scale 26 to measure the relative positions of that part of the leg above the knee and that part of the leg below the knee.

Figure 5:
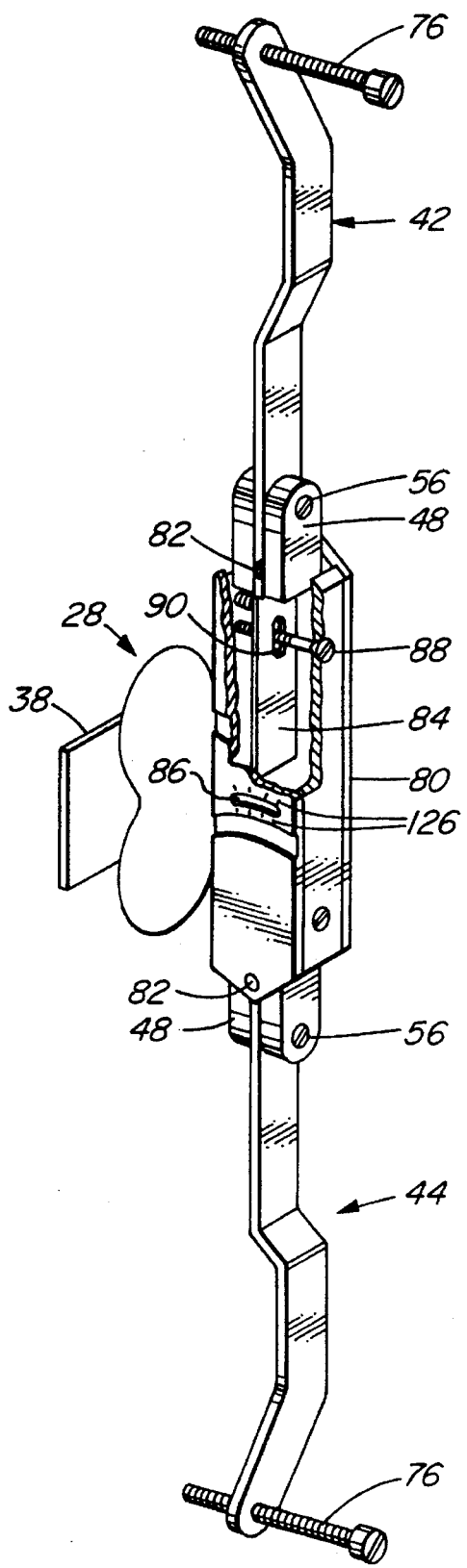
FIG. 5 illustrates a further embodiment of the invention.

The embodiment of FIG. 5 differs only in detail from that of FIGS. 1 to 4 and, where appropriate, the same reference numerals are used. In FIG. 5 the body comprises a box 80 and the pivot points are defined by pins 82 extending through the box 80. The markers are provided by extensions 84 of the limbs 42 and 44 and read on scales 126 marked at an opening 86 formed in a wall of the box 80. The box 80 is formed of flat sheets secured by screws 88. The extensions 84 are formed with openings 90 so that their movement is not inhibited by the screws 88. Use of the embodiment of FIG. 5 is precisely as for the embodiment of FIGS. 1 to 4.

The present invention thus provides a gauge that is easy to use. It is extremely .accurate and can provide an historical account of adjustments made to a brace on a patient. The device can be made of aluminum or cast simply from plastic.

Although the foregoing invention has been described in some detail by way of illustration and example for purposes of clarity of understanding, it will be readily apparent to those of ordinary skill in the art in light of the teachings of this invention that certain changes and modifications may be made thereto without departing from the spirit or scope of the appended claims.

I claim:

1. A gauge to measure the lateral inclination of a part of a brace above a patient's knee relative to a part of the brace below the patient's knee, the brace including a hinge to allow flexing of the knee, the gauge comprising:

a calibrated body having opposed ends;

means to attach the calibrated body to the hinge of the brace;

first and second limbs extending from each of said opposed ends;

a pivotal joint to allow each limb to pivot relative to said calibrated body;

a reciprocable extension at a distal end of each limb, able to extend to contact said brace;

a marker extending from each of said limbs to indicate on said calibrated body the inclination of each limb;

whereby the extension can be reciprocated to contact the brace and a reading then made of each marker on the calibrated body to determine the inclination of each limb of the gauge.

2. A gauge as claimed in claim 1 in which the calibrated body is a box formed with an opening with calibrations at said opening.

3. A gauge as claimed in claim 1 in which the means to attach the calibrated body to the hinge of the brace comprises a shaped member shaped to seat on the hinge of the brace; and a bracket to extend around the hinge of the brace to maintain the shaped member in contact with the hinge.

4. A gauge as claimed in claim 2 in which the first and second limbs are mounted to the box by pivot pins, one at each end of the box.

5. A gauge as claimed in claim 2 in which the limbs each comprise a hub with a lever releasably attached to the hub.

6. A gauge as claimed in claim 5 in which each said lever is formed with a threaded opening at its distal end to receive a screw as the reciprocable extension.

7. A gauge as claimed in claim 5 in which each said lever extends inwardly of the hub to the opening of said body whereby the inclination may be read on the calibration.

8. A gauge as claimed in claim 1 in which the calibrated body is laminar.

9. A gauge as claimed in claim 8 with a boss at each end of said body to receive a limb.

10. A gauge as claimed in claim 9 in which each limb comprises a hub and a lever releasably attached to said hub.

11. A gauge as claimed in claim 8 in which each said lever is formed with a threaded opening at its distal end to receive a screw as the reciprocable extension.

12. A gauge as claimed in claim 8 in which each of said markers comprises a coil spring attached to said boss and extending to the calibration on said body.

13. A gauge as claimed in claim 12 in which the coil of the coil spring is housed between said boss and said hub.

14. A gauge as claimed in claim 13 in which there is a slot in said boss to anchor said coil spring.

* * * * *